United States Patent [19]

Shimasaki et al.

[11] Patent Number: 4,841,061
[45] Date of Patent: Jun. 20, 1989

[54] PROCESS FOR PRODUCING CYCLIC AMINES

[75] Inventors: Yuuji Shimasaki, Takatsuki; Michio Ueshima, Takarazuka; Hideaki Tuneki; Kimio Ariyoshi, both of Suita, all of Japan

[73] Assignee: Nippon Shokubai Kagaku Kogyo Co., Ltd., Osaka, Japan

[21] Appl. No.: 126,351

[22] Filed: Nov. 30, 1987

Related U.S. Application Data

[63] Continuation-in-part of Ser. No. 943,086, Dec. 18, 1986, abandoned.

[30] Foreign Application Priority Data

| Dec. 27, 1985 | [JP] | Japan | 60-292541 |
| Nov. 17, 1986 | [JP] | Japan | 61-271965 |
| Nov. 17, 1986 | [JP] | Japan | 61-271966 |
| Nov. 17, 1986 | [JP] | Japan | 61-271967 |
| Nov. 17, 1986 | [JP] | Japan | 61-271968 |
| Nov. 17, 1986 | [JP] | Japan | 61-271969 |
| Nov. 17, 1986 | [JP] | Japan | 61-271970 |

[51] Int. Cl.⁴ .............. C07D 203/02; C07D 295/02; B01J 27/18
[52] U.S. Cl. ................. 546/184; 502/202; 502/208; 502/209; 502/210; 502/211; 502/212; 502/213; 502/214; 548/579; 548/950; 548/954; 548/969
[58] Field of Search .......... 546/184; 548/579, 950, 548/954, 969; 502/208

[56] References Cited

U.S. PATENT DOCUMENTS

| 3,089,900 | 5/1963 | Vitcha et al. | 260/486 |
| 3,520,915 | 7/1970 | Kominami et al. | 260/465.9 |
| 3,845,156 | 10/1974 | Fahra, Jr. | 502/208 |
| 3,933,932 | 1/1976 | Vrieland et al. | 502/208 |
| 4,013,694 | 3/1977 | Fishel | 260/346.2 |
| 4,036,881 | 7/1977 | Brennan et al. | 502/213 |
| 4,068,077 | 1/1978 | Goetz et al. | 544/178 |
| 4,105,657 | 8/1978 | Dockner | 546/184 |
| 4,324,908 | 4/1982 | Grasseli et al. | 502/208 |
| 4,324,921 | 4/1982 | Arpe | 568/427 |
| 4,337,175 | 6/1982 | Ramirez | 502/340 |
| 4,338,471 | 7/1982 | Okemura | 568/802 |
| 4,366,089 | 12/1982 | Krabbenhoft | 502/213 |
| 4,376,732 | 3/1983 | Ramirez | 548/969 |
| 4,446,320 | 5/1984 | Eskinazi et al. | 544/106 |
| 4,464,539 | 8/1984 | Hashimoto et al. | 502/208 |
| 4,477,591 | 10/1984 | Ramirez | 502/354 |
| 4,507,402 | 3/1985 | Kukes | 502/208 |
| 4,578,517 | 3/1986 | Johnson et al. | 564/479 |
| 4,605,770 | 8/1986 | Ford et al. | 564/479 |
| 4,774,218 | 9/1988 | Shimasaki et al. | 502/202 |

FOREIGN PATENT DOCUMENTS

| 1332526 | 10/1973 | European Pat. Off. |
| 1332527 | 10/1973 | European Pat. Off. |
| 0227461 | 7/1987 | European Pat. Off. |
| 0228898 | 7/1987 | European Pat. Off. |
| 77234 | 6/1981 | Japan | 502/208 |
| 2121430 | 12/1983 | United Kingdom |

*Primary Examiner*—Paul E. Konopka
*Attorney, Agent, or Firm*—Sherman and Shalloway

[57] ABSTRACT

A process for producing a cyclic amine represented by the general formula

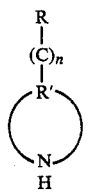
(II)

wherein each of R and R' is selected from hydrogen, a methyl group and an ethyl group, and n is an integer of 2 to 5, which comprises vapor-phase intramolecular dehydration reaction of an alkanolamine represented by the general formula

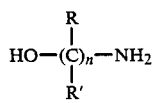
(I)

wherein R, R' and n are as defined above, said reaction being carried out in the presence of, as a catalyst, an oxide composition represented by the following formula

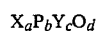

wherein X is at least one element selected from transition metal elements of Groups I through VIII, lanthanide elements, actinide elements and elements of Group IIIA in the periodic table, Si, Ge, Sn, Pb, Sb and Bi, P is phosphorus, Y is at least one element selected from alkali metal elements and alkaline earth metal elements, O is oxygen, the suffixes a, b, c and d are the atomic ratios of the elements X, P, Y and O respectively, and when a=1, b=0.01−6, preferably 0.05−3, and c=0−3, preferably 0.01−2, and d is a value determined by a, b and c and the state of bonding of the constituent elements.

13 Claims, No Drawings

PROCESS FOR PRODUCING CYCLIC AMINES

This application is a continuation-in-part application of Ser. No. 943,086 filed on Dec. 18, 1986, now abandoned.

This invention relates to a process for converting an alkanolamine of general formula (I) below into a cyclic amine of general formula (II) below using a novel catalyst for vapor-phase intramolecular catalytic dehydration reaction.

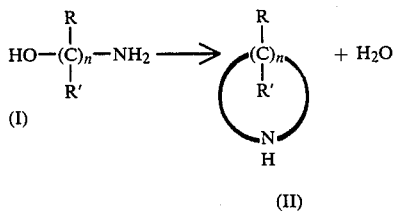

In the formulae, R and R' each represent hydrogen, a methyl group or an ethyl group, and n is an integer of 2 to 5.

Generally, cyclic amines of formula (II), particularly aziridine compounds (n=2), have good reactivity and react with compounds having various functional groups. Hence, various derivatives having amino groups can be produced from the cyclic amines. Furthermore, since they can be reacted while retaining rings, derivatives having ring-opening reactivity may be produced from them. Furthermore, polyamine-type polymers can be produced from them by ring-opening polymerization. Accordingly, these cyclic amines have extensive use. Derivatives of the cyclic amines are very useful compounds which are widely used in various industrial fields as, for example, textile finishing agents, antistatic agents, and materials for medicines and agricultural chemicals.

The present invention provides a process for the production of such useful cyclic amines by the intramolecular dehydration reaction of alkanolamines in the vapor-phase which is very advantageous in regard to productivity.

Known methods of converting alkanolamines into cyclic amines by dehydration reaction include, for example, the intramolecular cyclization of halo-alkylamines with concentrated alkalies (Gabriel method), and cyclization of alkanolamine sulfuric acid esters with hot concentrated alkalies (Wenker method). These methods, however, are not industrially satisfactory because the use of large amounts of alkalies as a concentrated solution reduces productivity and increases the percentages of the cost of the alkalies in the total expenditure of raw materials, and large amounts of inorganic salts of low useful values are formed as by-products.

In recent years, some attempts at dehydration reaction of monoethanolamine as the alkanolamine in the vapor phase in the presence of a catalyst to produce the corresponding cyclic amine, i.e. ethylenimine, continuously have been reported in contrast to the above liquid-phase methods. For example, Chemical Abstracts, 83, 163983 discloses the use of a tungsten oxide-type catalyst; U.S. Pat. No. 4,301,036 discloses the use of a catalyst comprising tungsten oxide and silicon; and U.S. Pat. Nos. 4,289,656, 4,337,175 and 4,477,591 disclose the use of niobium- or tantalum-type catalysts. With any of these catalysts, the conversion of monoethanolamine is low. Even when this conversion is relatively high, the proportion of products of side-reactions such as deammoniation reaction and dimerization reaction is high, and the selectivity of ethylenimine is low. Investigations of the present inventors have shown that these catalysts are deteriorated markedly within short periods of time, and are quite unsatisfactory in industrial practice.

The present inventors have extensively worked on a catalyst for the vapor-phase intramolecular dehydration reaction of alkanolamines, and have found that by using an oxide catalyst represented by the general formula $$X_a P_b Y_c O_d$$

wherein X is at least one element selected from transition metal elements of Groups I through VIII, lanthanide elements, actinide elements and elements of Group IIIA in the periodic table, Si, Ge, Sn, Pb, Sb and Bi, P is phosphorus, Y is at least one element selected from alkali metal elements and alkaline earth metal elements, O is oxygen, the suffixes a, b, c and d are the atomic ratios of the elements X, P, Y and O respectively, and when a=1, b=0.01−6, preferably 0.05−3, and c=0−3, preferably 0.01−2, and d is a value determined by a, b and c and the state of bonding of the constituent elements, as a catalyst, alkanolamines can be very conveniently dehydrated intramolecularly in the vapor phase to give the desired cyclic amines in high selectivities and high yields stably over a long period of time.

Examples of the element X are B, Al, Ga, Tl, Si, Sn, Sb, Bi, Sc, Cu, Zn, Cd, Y, Ti, Zr, Nb, Mo, Ta, W, Mn, Fe, Ni, La, Ce, Eu and Th. Examples of the element Y are Li, Na, K, Rb, Cs, Mg, Ca, Sr and Ba.

In the vapor-phase intramolecular dehydration reaction in which the catalyst of this invention is used, alkanolamines represented by the general formula

wherein R and R' are each selected from hydrogen, a methyl group and an ethyl group, and n is an integer of 2 to 5, are suitable as the starting material. Specific examples of the alkanolamines are (a) monoethanolamine, (b) isopropanolamine, (c) 3-amino-1-propanol, (d) 5-amino-1-pentanol, and (e) 2-amino-1-butanol. These examples, however, are not limitative.

These amines are converted to cyclic amines of the general formula

wherein R, R' and n are as defined for formula (I), by using the aforesaid catalyst. For example, the compound (a) is converted into ethylenimine; the compound (b), into 2-methyl-ethylenimine; the compound (c), into azetidine; the compound (d), into piperidine; and the compound (e), into 2-ethyl-ethylenimine, all in high conversions and high selectivities stably over long periods of time.

Raw materials used for preparation of the catalyst of this invention are as follows. As sources of the X and Y elements, their metals and their oxides, hydroxides, halides, and salts (nitrates, carbonates, sulfates, etc.) may be used. As a source of phosphorus, there may be used various phosphoric acids such as orthophosphoric acid, pyrophosphoric acid, meta-phosphoric acid, phophorous acid and polyphosphoric acid, salts of these phosphoric acids (e.g., ammonium ortho-phosphate, sodium ortho-phosphate, etc.), and phosphorus pentoxide. As sources of the elements X and Y and phosphorus, salts between the element X or Y and various phosphoric acids may also be used.

There is no particular limitation on a method of preparing the catalyst used in this invention, and ordinary methods may be used. For example, they include (1) a method which comprises dissolving or suspending raw materials for the element X, the element Y and phosphorus in water, concentrating the solution or suspension by heating with stirring, drying the concentrate, molding it and further calcining it, (2) a method which comprises dissolving raw materials for the X and Y components in water, adding the phosphoric acid or its salt to the solution, optionally adjusting the pH of the solution, forming a precipitate from the solution, filtering the precipitate, washing it with water, and then drying, molding and calcining it, and (3) a method which comprises mixing oxides or hydroxides of the elements X and Y with the phosphoric acid or its salt, molding the mixture after adding a suitable molding aid (such as water or alcohol), drying the molded product and calcining it.

Such catalysts may be used as supported on a known inert carrier. Preferred examples of such a carrier are silica, alumina, silicon carbide and diatomaceous earth.

The calcination temperature for the catalyst, which may be varied depending upon the types of the raw materials used, is 300° to 1,500° C., preferably 400° to 1,200° C.

These catalysts show much higher activity than conventional known catalysts when used in the vapor-phase intramolecular dehydration reaction of alkanolamines in accordance with this invention. The selectivity of the desired cyclic amine is very high. Even when this reaction is continuously carried out for a long period of time, the catalysts do not show an appreciable deterioration in activity. Accordingly, the problem of deterioration within a short time, which is most cumbersome in industrial practice, can be fully overcome by these catalysts.

Incidentally, it has been found that the activity and selectivity of the catalyst of this invention are much higher than those of known catalysts for synthesis of ethylenimine from monoethanolamine (for example, the $WO_3$-$SiO_2$ catalyst and the $Nb_2O_5$-$BaO$ catalyst disclosed respectively in Chemical Abstracts, 83, 163983 and U.S. Pat. No. 4,337,175).

No detailed reason has yet been able to be assigned to the fact that these catalysts exhibit very superior performance in the vapor-phase dehydration reaction of alkanolamines to cyclic amines. However, it may be considered as due to the cooperative action of acid sites and basic sites existing on the surface of the catalysts. The element X controls the acid strength of the acid sites by phosphoric acid and also produces basic sites, thereby creating a surface condition suitable for the present reaction on the catalysts. The element Y exercises a subtle control of the acid and basic sites on the catalyst surface and further increases the selectivity of the desired cyclic amine. Thus, the reaction proceeds effectively on the catalysts by the cooperative action of the acid and base. At the same time, desorption of the product from the catalysts becomes smooth, and the deactivation of the catalysts by poisoning is suppressed. Consequently, the desired cyclic amine can be produced very stably over a long period of time in a high conversion and a high selectivity without involving a reduction in selectivity which is seen to result from an increase in conversion in known conventional catalysts for the same reaction.

The reactor for use in carrying out the vapor-phase intramolecular dehydration reaction of alkanolamines using these catalyst may be of a fixed bed type, a fluidized bed type, or a moving bed type. As required, the starting alkanolamine may be diluted with an inert gas such as nitrogen, helium or argon to a concentration of 1 to 80% by volume, preferably 2 to 50% by volume, prior to submitting to the reaction. To inhibit side reactions, ammonia or water may be fed together with the alkanolamine. The reaction can usually be carried out under atmospheric pressure, but as required, it may be performed under elevated or reduced pressure. The reaction temperature, which varies depending upon the types of the starting material, is within the range of 300° to 600° C. The suitable space velocity of the starting material, which varies depending upon the type of the starting material and the concentration of the starting material, is 100 to 40,000 $hr^{-1}$, preferably 500 to 20,000 $hr^{-1}$.

The following examples illustrate the present invention more specifically. In these examples, the conversion, selectivity and one-pass yield are used in accordance with the following definitions.

Conversion (mole %) =

$$\frac{\text{Moles of the alkanolamine consumed}}{\text{Moles of the alkanolamine fed}} \times 100$$

Selectivity (mole %) =

$$\frac{\text{Moles of the cyclic amine formed}}{\text{Moles of the alkanolamine consumed}} \times 100$$

One-pass yield (mole %) =

$$\frac{\text{Moles of the cyclic amine formed}}{\text{Moles of the alkanolamine fed}} \times 100$$

EXAMPLE 1

Stannous oxide (40.4 g) was suspended in 100 ml of pure water, and 34.6 g of 85% by weight ortho-phosphoric acid was added. With thorough stirring, the mixture was concentrated by heating, and evaporated to dryness over a hot water bath. The product was dried at 120° C. for 12 hours in air, pulverized to a size of 9 to 5 mesh, and calcined at 600° C. for 2 hours to prepare a catalyst.

Twenty milliliters of the catalyst was filled in a stainless steel reaction tube having an inside diameter of 16 mm, and the reaction tube was immersed in a molten salt bath at 420° C. A starting gaseous mixture consisting of monoethanolamine and nitrogen in a volume ratio of 5:95 was passed through the reaction tube at a space velocity of 1500 $hr^{-1}$ (STP), and monoethanolamine was reacted continuously. The products obtained 2 hours and 50 hours after the start of the reaction were analyzed by gas chromatography. The results are shown in Table 1a.

EXAMPLE 2

A catalyst was prepared in the same way as in Example 1 except that 43.7 g of antimony trioxide was used instead of stannous oxide. Using the resulting catalyst, monoethanolamine and isopropanolamine were reacted respectively by the same method as in Example 1. The reaction conditions and the results are shown in Table 1a.

EXAMPLE 3

A catalyst was prepared in the same way as in Example 1 except that 9.0 g of silicon dioxide was used instead of stannous oxide, and the calcination was carried out 24 hours. Using the resulting catalyst, monoethanolamine and 3-amino-1-propanol were reacted respectively by the same method as in Example 1. The reaction conditions and the results are shown in Table 1a.

EXAMPLE 4

Aluminum nitrate nonahydrate (112.5 g) was dissolved in 300 ml of pure water, and a solution of 44.7 g of triammonium phosphate in 300 ml of pure water was added with stirring. The resulting precipitate was filtered, washed with water and dried at 120° C. for 12 hours. The resulting solid was pulverized to a size of 9 to 5 mesh, and calcined at 1,200° C. for 2 hours to prepare a catalyst. Using the resulting catalyst, monoethanolamine and 2-amino-1-butanol were reacted by the same method as in Example 1. The reaction conditions and the results are shown in Table 1a.

EXAMPLE 5

Bismuth hydroxide (8.0 g) and 36.9 g of ammonium pyrophosphate were mixed in the form of a powder, and then kneaded well with a small amount of water. The mixture was molded into pellets having a diameter of 3 mm and a length of 3 mm, dried at 120° C. for 12 hours in air, and calcined at 800° C. and then for 24 hours to prepare a catalyst. Using the resulting catalyst, monoethanolamine and 5-amino-1-pentanol were reacted by the same method as in Example 1. The reaction conditions and the results are shown in Table 1a.

EXAMPLE 6

A catalyst was prepared in the same way as in Example 1 except that 191.1 g of thallous oxide was used instead of stannous oxide. Using the resulting catalyst, monoethanolamine was reacted by the same method as in Example 1. The reaction conditions and the results are shown in Table 1a.

EXAMPLE 7

A catalyst was prepared in the same way as in Example 1 except that 11.7 g of aluminum hydroxide and 9.0 g of silicon dioxide were used instead of stannous oxide, and the calcination was carried out for 24 hours. Using the resulting catalyst, monoethanolamine was reacted by the same method as in Example 1. The reaction conditions and the results are shown in Table 1a.

EXAMPLE 8

Forty grams of the catalyst obtained in Example 2 was added to a solution of 10.2 g of thallous hydroxide in 50 ml of water. The mixture was evaporated to dryness over a hot water bath, dried at 120° C. for 12 hours in air, and calcined at 500° C. for 4 hours to prepare a catalyst. Using the resulting catalyst, monoethanolamine was reacted by the same method as in Example 1. The rection conditions and the results are shown in Table 1a.

EXAMPLE 9

A catalyst was prepared in the same way as in Example 1 except that 48.8 g of zinc oxide was used instead of stannous oxide. Using the resulting catalyst, monoethanolamine was reacted by the same method as in Example 1. The reaction conditions and the results are shown in Table 1a.

EXAMPLE 10

A catalyst was prepared in the same way as in Example 1 except that 33.9 g of yttruium oxide was used instead of stannous oxide. Using the resulting catalyst, monoethanolamine and isopropanolamine were reacted respectively by the same method as in Example 1. The reaction conditions and the results are shown are shown in Table 1a.

EXAMPLE 11

A catalyst was prepared in the same way as in Example 1 except that 33.9 g of niobium pentoxide was used instead of stannous oxide. Using the resulting catalyst, monoethanolamine and 3-amino-1-propanol were reacted respectively by the same method as in Example 1. The reaction conditions and the results are shown in Table 1a.

EXAMPLE 12

Zirconyl nitrate (40.1 g) was dissolved in 300 ml of water, and a soluti of 44.7 g of triammonium phosphate in 300 ml of water was added with stirring. The resulting precipitate was filtered, washed with water, dried overnight at 120° C. in air, pulverized to a size of 9 to 5 mesh, and calcined at 1200° C. for 2 hours to prepare a catalyst. Using the resulting catalyst, monoethanolamine and 2-amino-1-butanol were reacted respectively by the same method as in Example 1. The reaction conditions and the results are shown in Table 1a.

EXAMPLE 13

Manganese hydroxide (26.7 g), 21.6 g of ferrous oxide and 36.9 g of ammonium pyrophosphate were mixed in the form of a powder, and then kneaded well with a small amount of water. The mixture was molded into pellets, 3 mm in diameter and 3 mm in length, dried at 120° C. for 12 hours in air, and calcined at 800° C. for 4 hours in a stream of nitrogen to prepare a catalyst. Using the resulting catalyst, monoethanolamine and 5-amino-1-pentanol were reacted respectively by the same method as in Example 1. The reaction conditions and the results are shown in Table 1a.

EXAMPLE 14

A catalyst was prepared in the same way as in Example 1 except that 75.9 g of titanium oxide and 3.6 g of cuprous oxide were used instead of stannous oxide. Using the resulting catalyst, monoethanolamine was reacted by the same method as in Example 1. The reaction conditions and the results are shown in Table 1a.

EXAMPLE 15

Cadmium oxide (15.4 g) was added to a solution of 102.1 g of phosphotungstic acid nonacosahydrate in 100 ml of pure water, and the mixture was evaporated to dryness over a hot water bath. The product was dried at 120° C. for 12 hours in air, pulverized to a size of 9 to 5 mesh, and calcined at 600° C. for 2 hours to prepare a catalyst. Using the resulting catalyst, monoethanolamine was reacted by the same method as in Example 1. The reaction conditions and the results are shown in Table 1a.

EXAMPLE 16

A catalyst was prepared in the same way as in Example 1 except that 49.2 g of cerous oxide was used instead of stannous oxide. Using the resulting catalyst, monoethanolamine was reacted by the same method as in Example 1. The reaction conditions and the results are shown in Table 1a.

EXAMPLE 17

A catalyst was prepared in the same way as in Example 1 except that 79.2 g of thorium oxide was used instead of stannous oxide. Using the resulting catalyst, monoethanolamine and isopropanolamine were reacted respectively by the same method as in Example 1. The reaction conditions and the results are shown in Table 1a.

EXAMPLE 18

Lanthanum nitrate hexahydrate (130.3 g) was dissolved in 300 ml of pure water, and a solution of 44.7 g of triammonium phosphate in 300 ml of pure water was added to the solution with stirring. The resulting precipitate was filtered, washed with water, dried at 120° C. for 12 hours, pulverized to a size of 9 to 5 mesh, and calcined at 800° C. for 2 hours to prepare a catalyst. Using the resulting catalyst, monoethanolamine and 2-amino-1-butanol were reacted by the same method as in Example 1. The reaction conditions and the results are shown in Table 1a.

EXAMPLE 19

Cerium nitrate hexahydrate (117.3 g) and 6.69 g of europium chloride were dissolved in 300 ml of pure water, and a solution of 44.7 g of triammonium phosphate in 300 ml of pure water was added to the solution with stirring. The resulting precipitate was filtered, washed with water, and dried at 120° C. for 12 hours. The solid was pulverized to a size of 9 to 5 mesh, and calcined at 800° C. for 2 hours to prepare a catalyst. Using the resulting catalyst, monoethanolamine, 3-amino-1-butanol and 5-amino-1-pentanol were respectively reacted by the same method as in Example 1. The reaction conditions and the results are shown in Table 1a.

EXAMPLE 20

A catalyst was prepared in the same way as in Example 1 except that 24.6 g of cerous oxide and 39.6 g of thorium oxide were used instead of stannous oxide. Using the resulting catalyst, monoethanolamine was reacted by the same method as in Example 1. The reaction conditions and the results are shown in Table 1a.

EXAMPLE 21

Antimony trioxide (43.7 g) was suspended in 100 ml of pure water, and 34.6 g of 85% by weight ortho-phosphoric acid was added. With thorough stirring, the mixture was concentrated by heating, and evaporated to dryness over a hot water bath. The product was dried at 120° C. for 12 hours in air, and calcined at 600° C. for 2 hours. A solution of 12 g of sodium hydroxide in 40 ml of water was added to the resulting solid. The mixture was evaporated to dryness over a hot water bath, dried at 120° C. for 12 hours, pulverized to a size of 9 to 5 mesh, and calcined at 500° C. for 2 hours to prepare a catalyst. Using the resulting catalyst, monoethanolamne was reacted by the same method as in Example 1. The reaction conditions and the results are shown in Table 1b.

EXAMPLE 22

A catalyst was prepared in the same way as in Example 21 except that 15.4 g of rubidium hydroxide was used instead of sodium hydroxide. Using the resulting catalyst, monoethanolamine and isopropanolamine were reacted by the same method as in Example 1. The reaction conditions and the results are shown in Table 1b.

EXAMPLE 23

A solution of 12.6 g of lithium hydroxide monohydrate in 200 ml of water was added to 72.5 g of stannous pyrophosphate, and the mixture was evaporated to dryness over a hot water bath. The resulting solid was dried at 120° C. for 12 hours in air, pulverized to a size of 9 to 5 mesh, and calcined at 500° C. for 2 hours to prepare a catalyst. Using the resulting catalyst, monoethanolamine and 3-amino-1-propanol were reacted respectively by the same method as in Example 1. The reaction conditions and the results are shown in Table 1b.

EXAMPLE 24

Aluminum nitrate nonahydrate (112.5 g) was dissolved in 300 ml of pure water, and a solution of 44.7 g of triammonium phosphate in 300 ml of pure water was added to the solution with stirring. The resulting precipitate was filtered and washed with water, and a solution of 2.25 g of cesium hydroxide in 10 ml of water was added. They were well kneaded, and dried at 120° C. for 12 hours. The resulting solid was pulverized to a size of 9 to 5 mesh, and calcined at 1000° C. for 2 hours to prepare a catalyst. Using the resulting catalyst, monoethanolamine and 2-amino-1-butanol were reacted by the same method as in Example 1. The reaction conditions and the results are shown in Table 1b.

EXAMPLE 25

A catalyst was prepared in the same way as in Example 24 except that 9.2 g of barium oxide was used instead of cesium hydroxide. Using the resulting catalyst, monoethanolamine and 5-amino-1-pentanol were reacted respectively by the same method as in Example 1. The reaction conditions and the results are shown in Table 1b.

EXAMPLE 26

A catalyst was prepared in the same way as in Example 21 except that 9 g of silicon dioxide was used instead of antimony trioxide, 16.8 g of potassium hydroxide was used instead of sodium hydroxide, and the precalcination was carried out for 24 hours. Using the resulting catalyst, monoethanolamine was reacted by the same method as in Example 1. The reaction conditions and the results are shown in Table 1b.

EXAMPLE 27

A catalyst was prepared in the same way as in Example 21 except that 192.5 g of thallous oxide was used instead of antimony trioxide, and 0.36 g of sodium hydroxide and 0.92 g of rubidium hydroxide were used instead of 12 g of sodium hydroxide. Using the resulting catalyst, monethanolamine was reacted by the same method as in Example 1. The reaction conditions and the results are shown in Table 1b.

EXALMPLE 28

Aluminum oxide (14.5 g), 2.19 g of antimony trioxide, 36.9 g of ammonium hydrogen phosphate and 8.77 g of cesium nitrate were mixed in the form of a powder, and well kneaded with a small amount of water. The mixture was molded into pellets, 3 mm in diameter and 3 mm in length, dried at 120° C. for 12 hours, and calcined at 1000° C. for 24 hours to prepare a catalyst. Using the resulting catalyst, monoethanolamine was reacted by the same method as in Example 1. The reaction conditions and the results are shown in Table 1b.

EXAMPLE 29

A catalyst was prepared in the same way as in Example 21 except that 48.8 g of zinc oxide was used instead of antimony trioxide and 1.2 g of sodium hydroxide was used instead of 12 g of sodium hydroxide. Using the resultihg catalyst, monoethanolamine was reacted by the same method as in Example 1. The reaction conditions and the results are shown in Table 1b.

Example 30

A catalyst was prepared in the same way as in Example 29 except that 1.54 g of rubidium hydroxide was used instead of sodium hydroxide. Using the resulting catalyst, monoethanolamine and isopropanolamine were reacted respectively by the same method as in Example 1. The reaction conditions and the results are shown in Table 1b.

EXAMPLE 31

A solution of 12.6 g of lithium hyroxide monohydrate in 200 ml of water was added to 43.0 g of ferrous pyrophosphate octahydrate, and the mixture was evaporated to dryness over a hot water bath. The solid product was dried at 120° C. for 12 hours, pulverized to a size of 9 to 5 mesh, and calcined at 500° C. for 2 hours to prepare a catalyst. Using the resulting catalyst, monoethanolamine and 3-amino-1-propanol were reacpectively by the same method as in Example 1. The reaction conditions and the results are shown in Table 1b.

EXAMPLE 32

Zirconyl nitrate (40.1 g) was dissolved in 300 ml of pure water, and a solution of 44.7 g of triammonium phosphate in 300 ml of pure water was added to the solution with stirring. The resulting precipitate was filtered and washed with water, and a solution of 12 g of sodium hydroxide in 20 ml of water was added, and they were well kneaded. The mixture was dried at 120° C. for 12 hours, pulverized to a size of 9 to 5 mesh, and calcined at 1000° C. for 2 hours to prepare a catalyst. Using the resulting catalyst, monoethanolamine and 2-amino-1-butanol were reacted respectively by the same method as in Example 1. The reaction conditions and the results are shown in Table 1b.

EXAMPLE 33

A catalyst was prepared in the same way as in Example 32 except that 23.0 g of barium oxide was used instead of sodium hydroxide. Using the resulting catalyst, monoethanolamine and 5-amino-1-pentanol were reacted respectively by the same method as in Example 1. The reaction conditions and the results are shown in Table 1b.

EXAMPLE 34

A catalyst was prepared in the same way as in Example 21 except that 19.9 g of niobium oxide, 12.0 g of titanium dioxide and 0.21 g of cuprous oxide were used instead of antimony trioxide, 8.4 g of potassium hydroxide was used instead of sodium hydroxide, and the precalcination at 600° C. was carried out for 24 hours. Using the resulting catalyst, monoethanolamine was reacted by the same method as in Example 1. The reaction conditions and the results are shown in Table 1b.

EXAMPLE 35

Phosphotungstic acid nonacosahydrate (170.1 g) was dissolved in 200 ml of water, and a solution of 29.2 g of cesium nitrate in 200 ml of water was added. The resulting precipitate was filtered and washed with water and well kneaded with 0.318 g of sodium carbonate. The mixture was dried at 120° C. for 12 hours, pulverized to a size of 9 to 5 mesh, and calcined at 500° C. for 2 hours to prepare a catalyst. Using the resulting catalyst, monoethanolamine was reacted by the same method as in Example 1. The reaction conditions and the results are shown in Table 1b.

EXAMPLE 36

Yttrium oxide (30.5 g), 2.1 g of manganese oxide, 39.6 g of ammonium hydrogen phosphate and 17.5 g of cesium nitrate were mixed in the form of a powder, and well kneaded with a small amount of water. The mixture was molded into pellets, 3 mm both in diameter and length. The pellets were dried at 120° C. for 12 hours in air, and calcined at 800° C. for 24 hours to prepare a catalyst. Using the resulting catalyst, monoethanolamine as reacted by the same method as in Example 1. The reaction conditions and the results are shown in Table 1b.

EXAMPLE 37

A catalyst was prepared in the same way as in Example 21 except that 49.2 g of cerous oxide was used instead of antimony trioxide. Using the resulting catalyst, monoethanolamine was reacted by the same method as in Example 1. The reaction conditions and the results are shown in Table 1b.

EXAMPLE 38

A catalyst was prepared in the same way as in Example 21 except that 79.2 g of thorium oxide was used instead of antimony trioxide. Using the resulting catalyst, monoethanolamine and isopropanolamine were reacted respectively by the same method as in Example 1. The reaction conditions and the results are shown in Table 1b.

EXAMPLE 39

Lanthanum nitrate hexahydrate (130.3 g) was dissolved in 300 ml of pure water, and a solution of 44.7 g of triammonium phosphate in 300 ml of pure water was added to the solution with stirring. The resulting precipitate was filtered and washed with water, and a solution of 22.5 g of cesium hydroxide in 20 ml of water was added. They were well kneaded, and dried at 120° C. for 12 hours. The resulting solid was pulverized to a size of 9 to 5 mesh, and calcined at 800° C. for 2 hours. Using the resulting catalyst, monoethanolamine and 2-amino-1-butanol were reacted respectively by the same method as in Example 1. The reaction conditions and the results are shown in Table 1b.

EXAMPLE 40

A catalyst was prepared in the same way as in Example 39 except that 117.3 g of cerium nitrate hexahydrate and 6.69 g of europium chloride were used instead of lanthanum nitrate and 8.4 g of potassium hydroxide and 9.5 g of barium hydroxide octahydrate were used instead of cesium hydroxide. Using the resulting catalyst, monoethanolamine, 3-amino-1-butanol and 5-amino-1-pentanol were reacted by the same method as in Example 1. The reaction conditions and the results are shown in Table 1b.

EXAMPLE 41

A catalyst was prepared in the same way as in Example 21 except that 24.6 g of cerous oxide and 39.6 g of thorium oxide were used instead of antimony trioxide. Using the resulting catalyst, monoethanolamine was reacted by the same method as in Example 1. The reaction conditions and the results are shown in Table 1b.

COMPARATIVE EXAMPLE 1

A silicon carbide carrier (60 ml) was added to 100 g of a 30% by weight aqueous solution of ortho-phosphoric acid, and the mixture was evaporated to dryness over a hot water bath and dried at 120° C. for 12 hours. The resulting solid was calcined at 450° C. for 2 hours to prepare a catalyst. Using the resulting catalyst, monoethanolamine and 2-amino-1-butanol were reacted respectively by the same method as in Example 1. The reaction conditions and the results are shown in Table 2.

COMPARATIVE EXAMPLE 2

Silicon carbide having a particle diameter of 5 mm (40 g) was immersed in 65.2 g of an aqueous solution of ammonium meta-tungstate (50% by weight as $WO_3$), and evaporated over a hot water bath. The product was dried at 150° C. for 1 hour in air, and calcined at 715° C. in air for 4 hours to prepare a catalyst precursor. The precursor was immersed in 50 ml of a 10% colloidal solution of silicon dioxide, and evaporated to dryness over a hot water bath. The product was dried at 150° C. for 1 hour in air, and subsequently calcined at 715° C. for 4 hours to give a supported catalyst ($W_{1.0}Si_{0.5}O_{4.1}$ in atomic ratio) containing 25.4% by weight of tungsten oxide and 3.3% by weight of silicon dioxide.

Using the resulting catalyst, monoethnolamine was reacted as in Example 1. The reaction conditions and the results are shown in Table 2.

This catalyst was prepared in accordance with Example 4 of U.S. Pat. No. 4,301,036.

COMPARATIVE EXAMPLE 3

Niobium pentachloride (5.0 g) was completely dissolved in 50 ml of water at 60° C. Aqueous ammonia was added to adjust the pH of the solution to 7.0. The solution was filtered, and washed with water. The resulting solid was dissolved in 80 ml of a 10% by weight aqueous solution of oxalic acid. Furthermore, 0.2 g of barium hydroxide octahydrate was added. Silicon carbide (60 ml) was immersed in the solution, and the mixture was evaporated to dryness at 80° C. The resulting product was calcined at 500° C. in air for 3 hours to give a supported catalyst containing 3.7% by weight of niobium pentoxide and 0.5% by weight of barium oxide ($Nb_{1.0}Ba_{0.1}O_{2.6}$ by atomic ratio). Using this catalyst, monoethanolamine was reacted under the reaction conditions described in Example 1. The reaction conditions and the results are shown in Table 2.

This catalyst was prepared in accordance with Example 3 of U.S. Pat. No. 4,477,591.

EXAMPLE 42

Boron oxide (34.8 g) was suspended in 100 ml of pure water, and 115.3 g of 85% by weight of ortho-phosphoric acid was added. With thorough stirring, the mixture was concentrated by heating, and evaporated to dryness on a hot water bath. The product was dried at 120° C. for 12 hours in air, pulverized to a size of 9 to 5 mesh, and calcined at 500° C. for 2 hours to prepare a catalyst.

Using this catalyst, monoethanolamine was reacted by the same method as in Example 1. The reaction conditions and the results are shown in Table 1b.

EXAMPLE 43

Gallium oxide (18.7 g) was suspended in 100 ml of pure water, and 64.2 g of 85% by weight ortho-phosphoric acid and 12.0 g of sodium hydroxide were added to the suspension. With thorough stirring, the mixture was concentrated by heating and evaporated to dryness over a hot water bath. The product was dried at 120° C. for 12 hours in air, pulverized to a size of 9 to 5 mesh, and calcined at 600° C. for 2 hours to prepare a catalyst.

Using this catalyst, monoethanolamine and isopropanolamine were individually reacted by the same method as in Example 1. The reaction conditions and the results are shown in Table 1b.

EXAMPLE 44

Indium oxide (55.5 g) was suspended in 100 ml of pure water, and 23.1 g of 85% by weight ortho-phosphoric acid and 7.8 g of cesium nitrate were added to the suspension. With thorough stirring, the mixture was concentrated by heating and evaporated to dryness over a hot water bath. The product was dried at 120° C. for 12 hours in air, pulverized to a size of 9 to 5 mesh, and calcined at 600° C. for 2 hours to prepare a catalyst.

Using this catalyst, monoethanolamine was reacted by the same method as in Example 1. The reaction conditions and the results are shown in Table 1b.

EXAMPLE 45

Germanium oxide (5.23 g) was suspended in 300 ml of pure water, and 17.3 g of 85% by weight ortho-phosphoric acid, 19.5 g of cesium nitrate and 100 g of diatomaceous earth were added to the suspension. With thorough stirring, the mixture was concentrated by heating and evaporated to dryness over a hot water bath. The product was dried at 120° C. for 12 hours in air, pulverized to a size of 9 to 5 mesh, and calcined at 700° C. for 2 hours to prepare a catalyst.

Using this catalyst, monoethanolamine was reacted by the same method as in Example 1. The reaction conditions and the results are shown in Table 1b.

EXAMPLE 46

Lead oxide (111.6 g) was suspended in 200 ml of pure water, and 38.5 g of 85% by weight ortho-phosphoric acid and 2.0 g of sodium hydroxide were added to the suspension. With thorough stirring, the mixture was concentrated by heating and evaporated to dryness over a hot water bath. The product was dried at 120° C. for 12 hours in air, pulverized to a size of 9 to 5 mesh, and calcined at 600° C. for 2 hours to prepare a catalyst.

Using this catalyst, monoethanolamine was reacted by the same method as in Example 1. The reaction conditions and the results are shown in Table 1b.

EXAMPLE 47

Tantalum pentoxide (84.0 g) and 1.38 g of scandium trioxide were suspended in 200 ml of pure water, and 23.0 g of 85% by weight ortho-phosphoric acid and 4.0 g of sodium hydroxide were added to the suspension. With thorough stirring, the mixture was concentrated by heating, and evaporated over a hot water bath. The product was dried at 120° C. for 12 hours in air, pulverized to a size of 9 to 5 mesh, and calcined at 800° C. for 2 hours to prepare a catalyst.

Using this catalyst, monoethanolamine was reacted by the same method as in Example 1. The reaction conditions and the results are shown in Table 1b.

EXAMPLE 48

A solution of 145.4 g of nickel nitrate in 200 ml of pure water was mixed with a solution of 88.3 g of ammonium paramolybdate in 200 ml of pure water, and 115.3 g of 85% by weight ortho-phosphoric acid and 24.3 g of strontium hydroxide were added to the mixture. With thorough stirring, the mixture was concentrated by heating, and evaporated to dryness over a hot water bath. The product was dried at 120° C. in air for 12 hours, pulverized to a size of 9 to 5 mesh, and calcined at 600° C. for 2 hours.

Using this catalyst, monoethanolamine and monoisopropanolamine were individually reacted by the same method as in Example 1. The reaction conditions and the results are shown in Table 1b.

EXAMPLE 49

Aluminum oxide (51.0 g) was suspended in 100 ml of pure water, and 115.3 g of 85% by weight ortho-phosphoric acid was added. With thorough stirring, the mixture was concentrated by heating, and evaporated to dryness on a hot water bath. The product was dried at 120° C. for 12 hours in air, and calcined at 600° C. for 2 hours to form a solid. The solid was pulverized, and 5.83 g of magnesium hydroxide and 14.8 g of calcium hydroxide were added. They were well kneaded with a small amount of water, and the mixture was dried at 120° C. for 12 hours in air, pulverized to a size of 9 to 5 mesh, and calcined at 900° C. for 2 hours.

Using this catalyst, monoethanolamine was reacted by the same method as in Example 1. The reaction conditions and the results are shown in Table 1b.

TABLE 1a

| Example | Catalyst composition (atomic ratio excepting oxygen) X | P | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|
| 1 | Sn = 1 | 1 | monoethanolamine | ethylenimine | 1,500 | 420 | 5 | 2 | 61.5 | 62.1 | 38.2 |
|   |        |   |                  |              |       |     |   | 50 | 60.0 | 63.6 | 38.2 |
| 2 | Sb = 1 | 1 | monoethanolamine | ethyleneimine | 12,000 | 400 | 5 | 2 | 72.3 | 60.0 | 43.4 |
|   |        |   | isopropanolamine | 2-methylethyleneimine | 12,000 | 400 | 5 | 2 | 75.1 | 62.1 | 46.6 |
| 3 | Si = 1 | 2 | monoethanolamine | ethylenimine | 20,000 | 400 | 5 | 2 | 62.2 | 61.5 | 38.3 |
|   |        |   | 3-amino-1-propanol | azetidine | 20,000 | 400 | 5 | 2 | 71.6 | 63.2 | 45.3 |
| 4 | Al = 1 | 1 | monoethanolamine | ethylenimine | 6,000 | 400 | 5 | 2 | 81.2 | 54.2 | 44.0 |
|   |        |   | 2-amino-1-butanol | 2-ethylethylenimine | 6,000 | 400 | 5 | 2 | 79.4 | 58.7 | 46.6 |
| 5 | Bi = 1 | 1 | monoethanolamine | ethylenimine | 6,000 | 400 | 5 | 2 | 67.3 | 54.9 | 36.9 |
|   |        |   | 5-amino-1-pentanol | piperidine | 6,000 | 400 | 5 | 2 | 72.2 | 60.4 | 43.6 |
| 6 | Tl = 1 | 0.333 | monoethanolamine | ethylenimine | 1,500 | 430 | 20 | 2 | 55.3 | 73.1 | 40.4 |
|   |        |   |                  |              |       | 430 |   | 50 | 52.9 | 74.5 | 39.4 |
| 7 | Al = 0.5 Si = 0.5 | 0.5 | monoethanolamine | ethylenimine | 10,000 | 400 | 5 | 2 | 73.2 | 53.5 | 39.2 |
| 8 | Sb = 0.8 Tl = 0.2 | 0.8 | monoethanolamine | ethylenimine | 1,500 | 440 | 40 | 2 | 51.2 | 70.1 | 35.9 |
| 9 | Zn = 1 | 0.5 | monoethanolamine | ethylenimine | 1,500 | 420 | 5 | 2 | 45.9 | 68.2 | 31.3 |
|   |        |   |                  |              |       |     |   | 50 | 46.2 | 68.0 | 31.4 |

TABLE 1a-continued

| Example | Catalyst composition (atomic ratio excepting oxygen) X | P | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mole %) | Selectivity of the cyclic amine (mole %) | One-pass yield of the cyclic amine (mole %) |
|---|---|---|---|---|---|---|---|---|---|---|---|
| 10 | Y = 1 | 1 | monoethanolamine | ethylenimine | 1,500 | 400 | 5 | 2 | 71.3 | 51.9 | 37.0 |
|  |  |  | isopropanolamine | 2-methylethyleneimine | 1,500 | 400 | 5 | 2 | 75.8 | 52.1 | 39.5 |
| 11 | Nb = 1 | 1 | monoethanolamine | ethylenimine | 10,000 | 400 | 5 | 2 | 81.3 | 42.2 | 34.3 |
|  |  |  | 3-amino-1-propanol | azetidine | 10,000 | 400 | 5 | 2 | 73.4 | 43.9 | 32.2 |
| 12 | Zr = 1 | 2 | monoethanolamine | ethylenimine | 12,000 | 400 | 5 | 2 | 82.6 | 39.9 | 33.0 |
|  |  |  | 2-amino-1-butanol | 2-ethylethyleneimine | 12,000 | 400 | 5 | 2 | 83.1 | 42.1 | 35.0 |
| 13 | Fe = 0.5 | 0.5 | monoethanolamine | ethylenimine | 3,000 | 400 | 5 | 2 | 85.3 | 40.2 | 34.3 |
|  | Mn = 0.5 |  | 5-amino-1-pentanol | piperidine | 3,000 | 400 | 5 | 2 | 86.2 | 43.3 | 37.3 |
| 14 | Ti = 0.95 | 0.3 | monoethanolamine | ethylenimine | 1,500 | 420 | 20 | 2 | 51.5 | 55.3 | 28.5 |
|  | Cu = 0.05 |  |  |  |  |  |  | 50 | 49.8 | 56.2 | 28.0 |
| 15 | W = 0.75 | 0.0625 | monoethanolamine | ethylenimine | 1,500 | 430 | 40 | 2 | 41.3 | 62.1 | 25.6 |
|  | Cd = 0.25 |  |  |  |  |  |  |  |  |  |  |
| 16 | Ce = 1 | 1 | monoethanolamine | ethylenimine | 6,000 | 400 | 5 | 2 | 62.3 | 61.2 | 38.1 |
|  |  |  |  |  |  |  |  | 50 | 60.8 | 62.3 | 37.9 |
| 17 | Th = 1 | 1 | monoethanolamine | ethylenimine | 6,000 | 400 | 5 | 2 | 58.3 | 62.1 | 36.2 |
|  |  |  | isopropanolamine | 2-methylethyleneimine | 6,000 | 400 | 5 | 2 | 61.3 | 64.2 | 39.4 |
| 18 | La = 1 | 1 | monoethanolamine | ethylenimine | 6,000 | 400 | 5 | 2 | 63.9 | 60.3 | 38.5 |
|  |  |  | 2-amino-1-butanol | 2-ethylethyleneimine | 6,000 | 400 | 5 | 2 | 65.2 | 61.9 | 40.4 |
| 19 | Ce = 0.9 | 1 | monoethanolamine | ethylenimine | 6,000 | 400 | 5 | 2 | 65.9 | 62.1 | 40.9 |
|  | Eu = 0.1 |  | 3-amino-1-propanol | azetidine | 6,000 | 400 | 5 | 2 | 66.8 | 60.2 | 40.2 |
|  |  |  | 5-amino-1-pentanol | piperidine | 6,000 | 400 | 5 | 2 | 71.8 | 71.3 | 51.2 |
| 20 | Ce = 0.5 | 1 | monoethanolamine | ethylenimine | 3,000 | 420 | 40 | 2 | 50.7 | 72.0 | 36.5 |
|  | Th = 0.5 |  |  |  |  |  |  |  |  |  |  |

TABLE 1b

| Example | Catalyst composition (atomic ratio excepting oxygen) X | Y | P | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mol %) | Selectivity of the cyclic amine (mole %) | One-pass yield of the cyclic amine (mole %) |
|---|---|---|---|---|---|---|---|---|---|---|---|---|
| 21 | Sb = 1 | Na = 1 | 1 | monoethanolamine | ethylenimine | 1,500 | 430 | 5 | 2 | 72.1 | 75.3 | 54.3 |
|  |  |  |  |  |  |  |  |  | 50 | 71.0 | 76.1 | 54.0 |
| 22 | Sb = 1 | Rb = 0.5 | 1 | monoethanolamine | ethylenimine | 1,500 | 430 | 5 | 2 | 75.1 | 74.0 | 55.6 |
|  |  |  |  | isopropanolamine | 2-methylethyleneimine | 1,500 | 430 | 5 | 2 | 77.2 | 76.3 | 58.9 |
| 23 | Sn = 1 | Li = 1 | 1 | monoethanolamine | ethylenimine | 1,500 | 430 | 5 | 2 | 80.1 | 69.2 | 55.4 |

TABLE 1b-continued

| Example | Catalyst composition (atomic ratio excepting oxygen) X | Y | P | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mol %) | Selectivity of the cyclic amine (mole %) | One-pass yield of the cyclic amine (mole %) |
|---|---|---|---|---|---|---|---|---|---|---|---|---|
|  |  |  |  | 3-amino-1-propanol | azetidine | 1,500 | 430 | 5 | 2 | 79.8 | 70.9 | 56.6 |
| 24 | Al = 1 | Cs = 0.05 | 1 | monoethanolamine | ethylenimine | 1,500 | 430 | 5 | 2 | 81.3 | 80.0 | 65.0 |
|  |  |  |  | 2-amino-1-butanol | 2-ethylethylenimine | 1,500 | 430 | 5 | 2 | 82.5 | 81.1 | 66.9 |
| 25 | Al = 1 | Ba = 0.2 | 1 | monoethanolamine | ethylenimine | 1,500 | 450 | 20 | 2 | 68.9 | 74.8 | 51.5 |
|  |  |  |  | 5-amino-1-pentanol | piperidine | 1,500 | 450 | 5 | 2 | 92.5 | 75.4 | 69.7 |
| 26 | Si = 1 | K = 2 | 2 | monoethanolamine | ethylenimine | 3,000 | 440 | 5 | 2<br>50 | 87.6<br>86.1 | 73.1<br>73.9 | 64.0<br>63.6 |
| 27 | Tl = 1 | Na = 0.01<br>Rb = 0.01 | 0.333 | monoethanolamine | ethylenimine | 1,500 | 440 | 40 | 2 | 59.8 | 83.2 | 49.8 |
| 28 | Al = 0.95<br>Sb = 0.05 | Cs = 0.15 | 1 | monoethanolamine | ethylenimine | 1,500 | 430 | 5 | 2 | 78.5 | 89.8 | 70.5 |
| 29 | Zn = 1 | Na = 0.05 | 0.5 | monoethanolamine | ethylenimine | 1,500 | 430 | 5 | 2<br>50 | 50.1<br>49.5 | 85.3<br>85.4 | 42.7<br>42.3 |
| 30 | Zn = 1 | Rb = 0.025 | 0.5 | monoethanolamine | ethylenimine | 1,500 | 430 | 5 | 2 | 58.2 | 81.3 | 47.3 |
|  |  |  |  | isopropanolamine | 2-methylethyleneimine | 1,500 | 430 | 5 | 2 | 57.3 | 82.6 | 47.3 |
| 31 | Fe = 1 | Li = 1.5 | 1 | monoethanolamine | ethylenimine | 1,500 | 430 | 5 | 2 | 50.1 | 81.3 | 40.7 |
|  |  |  |  | 3-amino-1-propanol | azetidine | 1,500 | 430 | 5 | 2 | 48.2 | 82.1 | 39.6 |
| 32 | Zr = 1 | Na = 2 | 2 | monoethanolamine | ethylenimine | 1,500 | 430 | 5 | 2 | 82.3 | 65.8 | 54.2 |
|  |  |  |  | 2-amino-1-butanol | 2-ethylethylenimine | 1,500 | 430 | 5 | 2 | 83.2 | 64.0 | 53.2 |
| 33 | Zr = 1 | Ba = 1 | 2 | monoethanolamine | ethylenimine | 1,500 | 430 | 5 | 2 | 85.2 | 60.3 | 51.4 |
|  |  |  |  | 5-amino-1-pentanol | piperidine | 1,500 | 430 | 5 | 2 | 88.9 | 70.1 | 62.3 |
| 34 | Nb = 0.5<br>Ti = 0.49<br>Cu = 0.01 | K = 0.5 | 1 | monoethanolamine | ethylenimine | 1,500 | 430<br>440 | 5<br>20 | 2<br>2 | 75.1<br>50.1 | 76.3<br>79.3 | 57.3<br>39.7 |
| 35 | W = 1 | Cs = 0.25<br>Na = 0.01 | 0.083 | monoethanolamine | ethylenimine | 1,500 | 430 | 5 | 2<br>50 | 67.1<br>65.9 | 85.5<br>84.0 | 57.4<br>55.4 |
| 36 | Y = 0.9<br>Mn = 0.1 | Cs = 0.3 | 1 | monoethanolamine | ethylenimine | 1,500 | 450 | 40 | 2 | 51.1 | 73.6 | 37.6 |
| 37 | Ce = 1 | Na = 1 | 1 | monoethanolamine | ethylenimine | 3,000 | 430 | 5 | 2<br>50 | 73.2<br>72.1 | 74.1<br>75.0 | 54.2<br>54.1 |
| 38 | Th = 1 | Na = 1 | 1 | monoethanolamine | ethylenimine | 3,000 | 430 | 5 | 2 | 70.9 | 75.4 | 53.5 |
|  |  |  |  | isopropanolamine | 2-methylethyleneimine | 3,000 | 430 | 5 | 2 | 71.3 | 76.1 | 54.3 |
| 39 | La = 1 | Cs = 0.5 | 1 | monoethanolamine | ethylenimine | 3,000 | 430 | 5 | 2 | 77.5 | 73.1 | 56.7 |
|  |  |  |  | 2-amino-1-butanol | 2-ethylethylenimine | 3,000 | 430 | 5 | 2 | 76.8 | 73.2 | 56.2 |
| 40 | Ce = 0.9<br>Eu = 0.1 | K = 0.5<br>Ba = 0.1 | 1 | monoethanolamine | ethylenimine | 3,000 | 440 | 20 | 2 | 60.1 | 79.8 | 48.0 |
|  |  |  |  | 3-amino-1-propanol | azetidine | 3,000 | 430 | 5 | 2 | 78.3 | 70.5 | 55.2 |

TABLE 1b-continued

| Example | Catalyst composition (atomic ratio excepting oxygen) X | Y | P | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mol %) | Selectivity of the cyclic amine (mole %) | One-pass yield of the cyclic amine (mole %) |
|---|---|---|---|---|---|---|---|---|---|---|---|---|
| | | | | 5-amino-1-pentanol | piperidine | 3,000 | 430 | 5 | 2 | 86.9 | 78.2 | 68.0 |
| 41 | Ce = 0.5 Th = 0.5 | Na = 1 | 1 | monoethanolamine | ethylenimine | 1,500 | 450 | 40 | 2 | 51.8 | 82.1 | 42.5 |
| 42 | B = 1 | | 1 | monoethanolamine | ethylenimine | 5,000 | 420 | 5 | 2 | 81.3 | 51.0 | 41.5 |
| 43 | Ga = 1 | Na = 1.5 | 3 | monoethanolamine | ethylenimine | 1,000 | 430 | 5 | 2 | 62.4 | 81.0 | 50.5 |
| | | | | isopropanolamine | 2-methylethylenimine | 1,000 | 420 | 5 | 2 | 55.1 | 78.5 | 43.3 |
| 44 | In = 1 | Cs = 0.1 | 0.5 | monoethanolamine | ethylenimine | 2,000 | 420 | 5 | 2 | 79.8 | 69.6 | 55.5 |
| 45 | Ge = 1 | Cs = 2 | 3 | monoethanolamine | ethylenimine | 1,000 | 420 | 5 | 2 | 85.2 | 73.7 | 62.8 |
| 46 | Pb = 1 | Na = 0.1 | 0.67 | monoethanolamine | ethylenimine | 1,000 | 430 | 5 | 2 | 79.1 | 76.1 | 60.2 |
| 47 | Ta = 0.95 Sc = 0.05 | Na = 0.25 | 0.5 | monoethanolamine | ethylenimine | 2,000 | 420 | 5 | 2 | 79.5 | 61.2 | 48.7 |
| 48 | Ni = 0.5 Mo = 0.5 | Sn = 0.2 | 1 | monoethanolamine | ethylenimine | 1,500 | 430 | 5 | 2 | 69.1 | 69.5 | 48.0 |
| | | | | monoisopropanolamine | 2-methylethylenimine | 1,500 | 420 | 5 | 2 | 61.7 | 71.4 | 44.1 |
| 49 | Al = 1 | Mg = 0.1 Cs = 0.2 | 1 | monoethanolamine | ethylenimine | 1,000 | 420 | 5 | 2 | 76.9 | 70.3 | 54.1 |

TABLE 1a

| Comparative Example | Catalyst Composition (atomic ratio excepting oxygen) | Starting alkanolamine (I) | Produced cyclic amine (II) | SV (hr$^{-1}$) | Reaction temperature (°C.) | Concentration of the starting material (vol. %) | Reaction time elapsed (hrs.) | Conversion of the alkanolamine (mol %) | Selectivity of the cyclic amine (mole %) | One-pass yield of the cyclic amine (mole %) |
|---|---|---|---|---|---|---|---|---|---|---|
| 1 | P$_{1.0}$ | monoethanolamine | ethylenimine | 1,500 | 400 | 5 | 2 | 95.2 | 5.1 | 4.9 |
| | | 2-amino-1-butanol | 2-ethylethylenimine | 1,500 | 400 | 5 | 2 | 96.3 | 6.3 | 6.1 |
| 2 | W$_{1.0}$Si$_{0.5}$ | monoethanolamine | ethylenimine | 1,500 1,500 | 350 350 | 5 5 | 2 10 | 65.8 21.5 | 21.0 19.2 | 13.8 4.1 |
| 3 | Nb$_{1.0}$Ba$_{0.1}$ | monoethanolamine | ethylenimine | 1,500 1,500 | 420 420 | 5 5 | 2 10 | 45.1 18.2 | 69.2 74.3 | 31.2 13.5 |

What is claimed is:

1. A process for producing a cyclic amine represented by the general formula

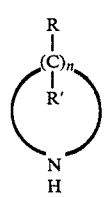

(II)

wherein each of R and R' is selected from hydrogen, a methyl group and an ethyl group, and n is an integer of 2 to 5, which comprises vapor-phase intramolecular dehydration reaction of an alkanolamine represented by the general formula

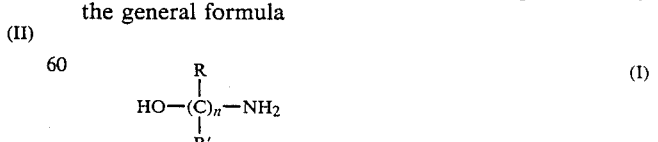

wherein R, R' and n are as defined above, said reaction being carried out in the presence of, as a catalyst, an oxide composition represented by the following formula $$X_aP_bY_cO_d$$

wherein X is at least one element selected from transition metal elements of Groups I through VIII, lanthanide elements, actinide elements and elements of Group IIIA in the periodic table, Si, Ge, Sn, Pb, Sb and Bi, P is phosphorus, Y is at least one element selected from alkali metal elements and alkaline earth metal elements, O is oxygen, the suffixes a, b, c and d are the atomic ratios of the elements X, P, Y and O, respectively, and when $a=1$, $b=0.01-6$, and $c=0-3$, and d is a value determined by a, b and c and the state of bonding of the constituent elements.

2. The process of claim 1 wherein in the formula representing the oxide composition, c is O, and X is at least one element selected from elements of Group IIIA, Si, Ge, Sn, Pb, Sb and Bi.

3. The process of claim 1 wherein in the formula representing the oxide composition, c is O, and X is at least one element selected from transition metal elements of Groups I through VIII.

4. The process of claim 1 wherein in the formula representing the oxide composition, c is O, and X is at least one element selected from lanthanide elements and actinide elements.

5. The process of claim 1 wherein in the formula representing the oxide composition, c is $0.001-3$, and X is at least one element selected from elements of Group IIIA, Si, Ge, Sn, Pb, Sb and Bi.

6. The process of claim 1 wherein in the formula representing the oxide compsoition, c is $0.001-3$, and X is at least one element selected from transition metal elements of Groups I through VIII.

7. The process of claim 1 wherein in the formula representing the oxide composition, c is $0.001-3$, and X is at least one element selected from lanthanide elements and actinide elements.

8. The process of claim 1 wherein $b=0.05-3$.

9. The process of claim 1 wherein $c=0.01-2$.

10. The process of claim 1 wherein $b=0.05-3$ and $c=0.01-2$.

11. The process of claim 1 wherein said vapor-phase intramolecular dehydration reaction is carried out at a temperature within the range of 300° to 600° C.

12. The process of claim 1 wherein the vapor-phase intramolecular dehydration reaction is carried out at a space velocity of from 100 to 40,000 $hr^{-1}$.

13. The process of claim 1 wherein the vapor-phase intramolecular dehydration reaction is carried out at atmospheric pressure.

* * * * *